United States Patent

Beriger et al.

Patent Number: 5,162,349
Date of Patent: Nov. 10, 1992

[54] NEMATOCIDAL AND FUNGICIDAL COMPOSITIONS

[75] Inventors: Ernst Beriger, Allschwil, Switzerland; Wolfgang Eckhardt, Lörrach, Fed. Rep. of Germany

[73] Assignee: Ciba-Geigy Corporation, Ardsley, N.Y.

[21] Appl. No.: 408,837

[22] Filed: Sep. 18, 1989

[30] Foreign Application Priority Data

Sep. 23, 1988 [CH] Switzerland ............. 3537/88
Feb. 24, 1989 [CH] Switzerland ............. 673/89

[51] Int. Cl.⁵ ............. C07D 417/04; C07D 413/04; A01N 43/82
[52] U.S. Cl. ............. 514/363; 514/364; 548/136; 548/144
[58] Field of Search ............. 548/136, 144; 514/363, 514/364

[56] References Cited

U.S. PATENT DOCUMENTS

| | | | |
|---|---|---|---|
| 3,770,754 | 11/1973 | Parsons | 548/132 |
| 4,094,014 | 9/1987 | Beriger | 514/363 |
| 4,454,147 | 6/1984 | Di Menna et al. | 514/363 |
| 4,894,380 | 1/1990 | Nyfeler | 514/340 |

FOREIGN PATENT DOCUMENTS

| | | | |
|---|---|---|---|
| 2254423 | 5/1974 | Fed. Rep. of Germany | 548/136 |
| 8802323 | 1/1978 | South Africa . | |
| 1429725 | 3/1976 | United Kingdom . | |

*Primary Examiner*—Robert Gerstl
*Attorney, Agent, or Firm*—Marla J. Mathias; Roberts. Edward McC.

[57] ABSTRACT

Mercapto-bis-[1,3,4-oxa- and -thiadiazoles]

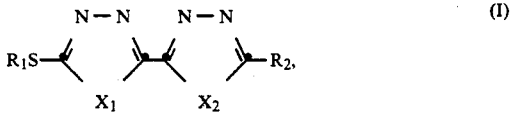

in which
$X_1$ and $X_2$ independently of one another are oxygen or sulfur, $R_1$ is hydrogen or $C_1$-$C_5$alkyl which is unsubstituted or substituted by halogen, $C_1$-$C_3$alkoxy or cyano; $C_3$-$C_7$alkenyl which is unsubstituted or substituted by halogen; or $C_3$-$C_7$alkynyl which is unsubstituted or substituted by halogen, $R^2$ is hydrogen, $C_1$-$C_5$alkyl, $C_1$-$C_3$alkoxy which is unsubstituted or substituted by halogen, $C_1$-$C_3$alkylthio which is unsubstituted or substituted by halogen, $C_3$-$C_7$alkenylthio which is unsubstituted or substituted by halogen, $C_3$-$C_7$alkynylthio which is unsubstituted or substituted by halogen, —SH, phenyl which is unsubstituted or substituted by halogen or

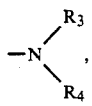

in which $R_3$ and $R_4$ are $C_1$-$C_3$alkyl, and processes for the preparation of the compounds of the formula I are described.

The compounds of the formula I have nematocidal and microbicidal properties. Nematocidal compositions which contain at least one active substance of the formula I as the active substance and furthermore processes for the use of the active substances and the compositions in combating nematodes and fungi which are harmful to plants are described.

40 Claims, No Drawings

NEMATOCIDAL AND FUNGICIDAL COMPOSITIONS

The present invention relates to novel substituted mercapto-bis-[1,3,4-oxa- and -thiadiazoles], their preparation and nematocidal and fungicidal compositions containing at least one of these compounds as the active substance. The invention furthermore relates to processes for the preparation of the active substances, their use and compositions for controlling nematodes, in particular nematodes which damage plants, and fungi, in particular soil-borne fungi which damage plants.

The mercapto-bis-[1,3,4-oxa- and -thiadiazoles] according to the invention are those of the general formula I

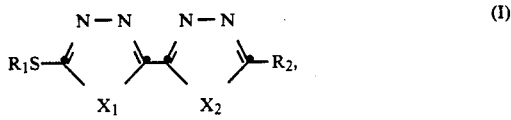

in which
- $X_1$ and $X_2$ independently of one another are oxygen or sulfur, $R_1$ is hydrogen or $C_1$–$C_5$alkyl which is unsubstituted or substituted by halogen, $C_1$–$C_3$alkoxy or cyano; $C_3$–$C_7$alkenyl which is unsubstituted or substituted by halogen; or $C_3$–$C_7$alkynyl which is unsubstituted or substituted by halogen,
- $R_2$ is hydrogen, $C_1$–$C_5$alkyl, $C_1$–$C_3$alkoxy which is unsubstituted or substituted by halogen, $C_1$–$C_3$alkylthio which is unsubstituted or substituted by halogen, $C_3$–$C_7$alkenylthio which is unsubstituted or substituted by halogen, $C_3$–$C_7$alkynylthio which is unsubstituted or substituted by halogen, —SH, phenyl which is unsubstituted or substituted by halogen or

in which $R_3$ and $R_4$ are $C_1$–$C_3$alkyl, and salts of these compounds.

Alkyl as an independent radical and as part of another group, such as alkoxy, is to be understood as meaning straight-chain and branched alkyl groups. These include the methyl, ethyl and normal and isomeric propyl, butyl and pentyl groups. Halogen-substituted alkyl is an alkyl radical which is mono- to perhalogenated, for example $CHCl_2$, $CH_2F$, $CCl_3$, $CH_2Cl$, $CHFCH_3$, $CH_2CH_2Br$, $CF_2CF_3$, $C_2Cl_5$, $CH_2Br$, $CHBrCl$ and the like, preferably $CHF_2$. Methylthio may be mentioned as an example of alkylthio, difluoromethylthio may be mentioned as an example of halogenoalkylthio and alkenyl is, for example, propen-1-yl, allyl, buten-1-yl, buten-2-yl or buten-3-yl as well as chains having several double bonds. Halogenoalkenyl is, for example, 3,4,4-trifluoro-3-buten-1-yl. 3,4,4-Trifluoro-3-buten-1-ylthio may be mentioned as a halogenoalkenylthio group and 4-chlorophenyl may be mentioned as a halogen-substituted phenyl. Alkynyl is, for example, propyn-2-yl, butyn-1-yl, butyn-2-yl, pentyn-4-yl and the like. Halogen is fluorine, chlorine, bromine or iodine, preferably fluorine, chlorine or bromine. Diethylamino, diisopropylamino and, preferably, dimethylamino may be mentioned as examples of dialkylamino radicals.

Examples of salt-forming acids are, amongst the inorganic acids, hydrohalic acids, such as hydrofluoric acid, hydrochloric acid, hydrobromic acid or hydroiodic acid, and furthermore sulfuric acid, phosphoric acid, phosphorous acid and nitric acid, and, amongst the organic acids, acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid or 2-acetoxybenzoic acid.

Oxadiazole and thiadiazole derivatives which are described as having a nematocidal action are already known. Thus, U.S. Pat. No. 3,770,754 discloses those compounds having a 1,2,4-position of the heteroatoms, whereas U.S. Pat. No. 4,454,147 describes 1,3,4-thiadiazole derivatives in which, in contrast to the compounds according to the invention, the heterocyclic radical is substituted by a chlorine atom instead of the mercapto groups. To date, these known compounds have not been able to satisfy completely the demands made on them in practice as nematicides. Oxadiazole derivatives having a fungicidal activity are furthermore described in German Offenlegungsschrift 2,361,613. However, none of these compounds which fall within the scope of the formula I according to the invention are mentioned expressly in this publication.

By providing the compounds of the formula I according to the invention, it has now been possible to make a useful contribution to controlling plant nematodes which cause considerable agricultural damage to plants. Harvest losses of crop plants, for example potatoes, cereals, beet, rape, cabbage, tobacco, soya bean, cotton and vegetables, and damage in tree nurseries and in ornamental plant growing can in this way be checked in a lasting manner. The compounds according to the invention are particularly distinguished here in effectively controlling soil nematodes which are root parasites, for example those of the genera Heterodera and Globodera (cyst-forming nematodes), Meloidogyne (root knot nematodes) and of the genera Radopholus, Pratylenchus, Tylenchulus, Longidorus, Trichodorus and Xiphinema. The nematode genera Ditylenchus (stem parasites), Aphelenchoides (leaf nematodes) and Anguina (blossom nematodes) can furthermore be effectively combated with the active substances according to the invention.

Particularly harmful nematode species of the genus Meloidogyne, for example *Meloidogyne incognita*, and of the genus Heterodera, for example *Heterodera glycines* (soya bean cyst nematode), and furthermore of the genus Globodera, for example *Globodera rostochiensis* (potato cyst nematode), as well as representatives of migrating endoparasites, for example *Pratylenchus penetrans* or *Radopholus similis*, and representatives of ectoparasites, for example Trichodorus spp. and Xiphinema spp., can preferably be controlled successfully using the active substances of the formula I.

Particularly harmful soil fungi of the genus Pythium, for example *Pythium ultimum*, of the genus Rhizoctonia, for example *Rhizoctonia solani*, and of the genus Fungi imperfecti, for example Cercospora, Basidomycetes, for example Puccinia, Ascomycetes, for example Erysiphe, and Oomycetes, for example Phytophthora or Plasmopara, can likewise preferably be combated successfully using the active substances of the formula I.

The novel active substances can be employed curatively, preventatively or systemically for controlling plant nematodes and soil fungi and for keeping plants healthy. During this use, they display a widely diverse activity against the various nematode and soil fungus species and thus meet requirements in practice. The nematocidal and fungicidal mode of action of the compounds according to the invention is advantageously accompanied by a low phytotoxicity, which particularly takes into account the generally desirable reduction in environmental pollution.

A nematocidal activity is detected and also determined by inhibition of the root knot formation on the treated crop plant in comparison with the untreated plant.

The action is described as "good" if the infestation of the treated plant is lower than 20% of the infestation of the untreated plant.

In the context of the present invention, preferred nematocidal active substances are those compounds of the formula I in which $R_2$ is hydrogen, $C_1$–$C_5$alkyl, alkylthio, difluoromethylthio, alkenylthio, 3,4,4-trifluoro-$R_3$ 3-buten-1-ylthio, SH, phenyl or

Preferred compounds of this group are those in which $R_1$ is methyl, difluoromethyl, trifluoromethyl, cyanomethyl, allyl, propargyl or 3,4,4-trifluoro-3-buten-1-yl and $R_2$ is hydrogen, methyl, difluoromethylthio, 3,4,4-trifluoro-3-buten-1-ylthio, SH, phenyl or dimethylamino.

Compounds of this group which are particularly preferred are those in which $R_1$ is difluoromethyl or 3,4,4-trifluoro-3-buten-1-yl.

Preferred individual compounds are 2-difluoromethylthio-5-(2-methyl-1,3,4-oxadiazol-5-yl)-1,3,4-oxadiazole, 2-(3,4,4-trifluoro-3-buten-1-ylthio)-5-(2-methyl-1,3,4-oxadiazol-5-yl)-1,3,4-oxadiazole, 2-difluoromethylthio-5-(2-methyl-1,3,4-oxadiazol-5-yl)-1,3,4-thiadiazole, 2-(3,4,4-trifluoro-3-buten-1-ylthio)-5-(2-methyl-1,3,4-oxadiazol-5-yl)-1,3,4-thiadiazole, 2-(3,4,4-trifluoro-3-buten-1-ylthio)-5-(2-methylthio-1,3,4-thiadiazol-5-yl)-1,3,4-thiadiazole and 2-(3,4,4-trifluoro-3-buten-1-yl-thio)-5-(2-methylthio-1,3,4-thiadiazol-5-yl)-1,3,4-oxadiazole, 2-(difluoromethylthio)-5-(2-methyl-1,3,4-oxadiazol-5-yl)-1,3,4-thiadiazole, 2-(3,4,4-trifluoro-3-buten-1-ylthio)-5-(2-methyl-1,3,4-oxadiazol-5-yl)-1,3,4-thiadiazole, 2-(3,4,4-trifluoro-3-buten-1-ylthio)-5-(2-mercapto-1,3,4-oxadiazol-5-yl)-1,3,4-thiadiazole, 2-(3,4,4-trifluoro-3-buten-1-ylthio)-5-[2-(3,4,4-trifluoro-3-buten-1-ylthio)-1,3,4-oxadiazol-5-yl]-1,3,4-thiadiazole, 2-(3,4,4-trifluoro-3-buten-1-ylthio)-5-(2-phenyl-1,3,4-oxadiazol-5-yl)-1,3,4-thiadiazole, 2-(3,4,4-trifluoro-3-buten-1-ylthio)-5-(2-phenyl-1,3,4-oxadiazol-5-yl)-1,3,4-oxadiazole, 2-(3,4,4-trifluoro-3-buten-1-ylthio)-5-(2-difluoromethylthio-1,3,4-oxadiazol-5-yl)-1,3,4-thiadiazole and 2-(3,4,4-trifluoro-3-buten-1-ylthio)-5-[2-(3,4,4-trifluoro-3-buten-1-ylthio)-1,3,4-oxadiazol-5-yl]-1,3,4-oxadiazole.

The compounds of the formula I are prepared according to the invention by a) reacting, in a condensation reaction, a compound of the formula II

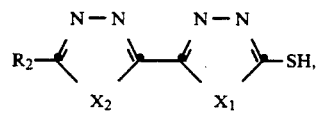

or a compound of the formula III

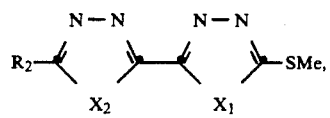

with a compound of the formula IV

Hal-$R_1$                 (IV)

in an inert solvent or solvent mixture at elevated temperature, if appropriate in the presence of a catalyst and if appropriate under elevated pressure, the reaction of a compound of the formula II proceeding in the presence of a base, or b) reacting, in an addition reaction, a compound of the formula II

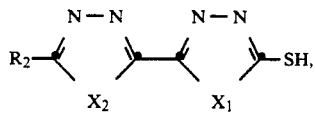

with a compound of the formula V

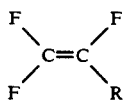

in an inert solvent or solvent mixture at elevated temperature, if appropriate in the presence of a catalyst and if appropriate under elevated pressure, this reaction leading to a compound of the formula Ie

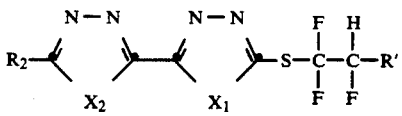

or to a compound of the formula If

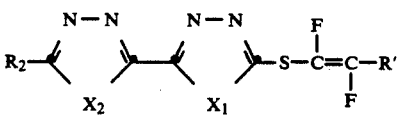

in which, in the abovementioned formulae II, III, Ie, If, IV and V, Me is an alkali metal or ammonium, Hal is halogen, preferably chlorine, bromine or iodine, and R' is fluorine or trifluoromethyl, whilst $R_1$ and $R_2$ are as defined under formula I.

Suitable solvents or diluents for the preparation of the active substances according to the invention are, for example, ethers and ether-like compounds, such as dialkyl ethers (diethyl ether, diisopropyl ether, tert-butyl methyl ether and the like), anisole, dioxane and tetrahydrofuran; aliphatic and aromatic hydrocarbons, such as benzene, toluene and petroleum ether; halogenated hydrocarbons, such as chlorobenzene, methylene chloride, chloroform, ethylene chloride, carbon tetrachloride and tetrachloroethylene; nitriles, such as acetonitrile and propionitrile; N,N-dialkylated amides, such as dimethylformamide; dimethyl sulfoxide; ketones, such as acetone, diethyl ketone and methyl ethyl ketone, as well as water and alcohols, for example methanol, ethanol, isopropanol or butanol; and quite generally mixtures of such solvents with one another.

Possible bases are organic and inorganic bases; for example, preferably tertiary amines, such as trialkylamines (trimethylamine, triethylamine, tripropylamine and the like), and oxides, hydroxides, carbonates and bicarbonates of alkali metals and alkaline earth metals (for example CaO, BaO, NaOH, KOH, Ca(OH)$_2$, KHCO$_3$, NaHCO$_3$, Ca(HCO$_3$)$_2$, K$_2$CO$_3$, Na$_2$CO$_3$ and the like), and furthermore acetates, for example CH$_3$COONa or CH$_3$COOK. Alkali metal alcoholates, for example sodium ethylate, sodium propylate, potassium tert-butylate or sodium methylate, are moreover also suitable as bases.

The addition of catalytic amounts of a crown ether, for example 18-crown-6 or 15-crown-5, has a favourable effect on the course of the reaction in the preparation processes. The catalytic use of tetraalkylamine salts, for example tetraalkylammonium chlorides or bromides, preferably tetra-n-butylammonium bromide, has furthermore proved to be advantageous for the same purpose. Alkali metal iodides, preferably potassium iodide, can moreover advantageously be employed as catalysts.

In the preparation processes, the reaction temperatures are 10° to 90° C., preferably 30° to 80° C. The pressure conditions during the course of the reaction are, as a rule, 1 to 20 bar, preferably 6 to 14 bar.

The starting compounds of the formula II are known in some cases and novel in others. The novel compounds of the formula IIa

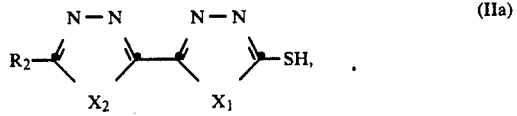

(IIa)

in which R$_2$, X$_1$ and X$_2$ are as defined under formula I, with the proviso that R$_2$ is other than hydrogen if X$_1$ and X$_2$ are sulfur, are intermediates for the preparation of useful nematocidal active substances and thus are part of the present invention.

The compounds of the formula IIa in which R$_2$, X$_1$ and X$_2$ are as defined under formula I, with the proviso that X$_1$ and X$_2$ are not simultaneously sulfur, may be mentioned in particular.

The starting compounds of the formula II can be prepared by known methods as follows:

a) The 2-mercapto-1,3,4-oxadiazoles can be obtained by adding carbon disulfide to a solution of the appropriately substituted hydrazide in alcoholic-aqueous potassium hydroxide and heating the reaction mixture for some hours. Alcohols, for example ethyl alcohol or n-amyl alcohol, are used here as the solvent. The free mercapto compounds are obtained by acidification of the potassium salts formed [cf. J.Am.Chem.Soc. 78, 4975–4978 (1956)]. The 2-mercapto-1,3,4-oxadiazoles can furthermore be obtained by reaction of the corresponding acyl hydrazide with thiophosgene in an inert solvent, for example dioxane [cf. J.Org.Chem. 26, 88–95 (1961)].

b) The 2-mercapto-1,3,4-thiadiazoles can be obtained by treatment of the appropriately substituted potassium acyldithiocarbazate with concentrated sulfuric acid at −5° to 10° C. [cf. J.prakt.Chem. 93, 49 (1916); J.Org.-Chem. 23, 1021 (1958); and J.Heterocycl.Chem. 19, 542–544 (1982)].

The invention also relates to compositions which contain the active substances of the formula I for controlling nematodes and fungi which are harmful to plants and for preventive protection from infestation of plants by nematodes and fungi.

The present invention moreover additionally includes the preparation of nematocidal and fungicidal compositions, which comprises intimate mixing of active substances of the formula I with one or more of the carriers and auxiliary ingredients described in this specification. It also includes a method of treating plants which comprises application of the compounds of the formula I or of the novel composition.

A preferred method for employing an active substance of the formula I or a nematocidal composition containing at least one of these active substances is introduction into the soil. In this procedure, the location of the plants is treated with a liquid or solid formulation.

However, the compounds of the formula I can also be applied to seeds (dressing/coating) by either soaking the seeds in a liquid formulation of the active substance or coating them with a solid formulation. In special cases, other types of application are moreover possible, for example controlled treatment of the plant stem, buds or leaves.

Active substances of the formula I are usually employed in the form of formulated compositions and can be applied to the area or plants to be treated at the same time as or successively with other active substances. These other active substances can also include other compositions used in agriculture which serve in their beneficial use for increasing production by promoting the growth of crop plants, such as fertilizers, herbicides, insecticides, fungicides, molluscicides and the like, or can be mixtures of several of these preparations, if appropriate together with other carriers, surfactants or other application-promoting additives conventionally used in the art of formulation.

Suitable carriers and additives can be solid or liquid and correspond to the expedient substances in the art of formulation, for example naturally occurring or regenerated mineral substances, solvents, dispersants, wetting agents, tackifiers, thickeners, binders or fertilizers.

The compounds of the formula I are employed in non-modified form or, preferably, together with the auxiliaries conventionally used in the art of formulation. They are processed in a known manner, for example, to emulsion concentrates, directly sprayable or dilutable solutions, dilute emulsions, wettable powders, soluble powders, dusts or granules, by encapsulation in, for example, polymeric substances. The use methods, such as spraying, dusting, scattering or watering, like the nature of the compositions, are chosen according to the intended aims and the given circumstances. Advantageous application amounts are in general 500 g to 6 kg of active substance (AS) per ha; preferably 1 to 4 kg of AS/ha.

The formulations, i.e. the compositions, preparations or combinations containing the active substance of the formula I and if appropriate a solid or liquid additive, are prepared in a known manner, for example by intimate mixing and/or grinding of the active substances with extenders, for example with solvents or solid carriers, and if appropriate with surface-active substances (surfactants).

Possible solvents are: aromatic hydrocarbons, preferably fractions $C_8$ to $C_{12}$, for example xylene mixtures or substituted naphthalenes, phthalic acid esters, such as dibutyl or dioctyl phthalate, aliphatic hydrocarbons, such as cyclohexane or paraffins, alcohols and glycols and ethers and esters thereof, such as ethanol, ethylene glycol and ethylene glycol monomethyl or monoethyl ether, ketones, such as cyclohexanone, strongly polar solvents, such as N-methyl-2-pyrrolidone, dimethyl sulfoxide or dimethylformamide, and if appropriate epoxidized vegetable oils, such as epoxidized coconut oil or soya oil; or water.

Solid carriers, for example for dusts and dispersible powders, which are as a rule used are naturally occurring rock powders, such as calcite, talc, kaolin, montmorillonite or attapulgite. It is also possible to add highly disperse silica or highly disperse absorbent polymers to improve the physical properties. Possible granular adsorptive granule carriers are porous grades, for example pumice, crushed brick, sepiolite or bentonite, and possible non-absorbent carrrier materials are, for example, calcite or sand. A large number of pregranulated materials of inorganic or organic nature, such as, in particular, dolomite or comminuted plant residues, can moreover be used.

Possible surface-active substances are, depending on the nature of the active substance of the formula I to be formulated, non-ionic, cationic and/or anionic surfactants having good emulsifying, dispersing and wetting properties. Surfactants are also to be understood as meaning surfactant mixtures.

Suitable anionic surfactants are both so-called water-soluble soaps and water-soluble synthetic surface-active compounds.

Soaps which may be mentioned are the alkali metal, alkaline earth metal or unsubstituted or substituted ammonium salts of higher fatty acids ($C_{10}$–$C_{22}$), for example the Na or K salts of oleic or stearic acid, or of naturally occurring fatty acid mixtures, which can be obtained, for example, from coconut oil or tallow oil. The fatty acid methyl laurate salts and modified and nonmodified phospholipids may furthermore also be mentioned.

However, so-called synthetic surfactants, in particular fatty sulfonates, fatty sulfates, sulfonated benzimidazole derivatives or alkylsulfonates, are more often used.

The fatty alcohol sulfonates or sulfates are as a rule in the form of alkali metal, alkaline earth metal or unsubstituted or substituted ammonium salts and have an alkyl radical having 8 to 22 C atoms, alkyl also including the alkyl part of acyl radicals, for example the Na or Ca salt of lignin-sulfonic acid, or dodecylsulfuric ester or of a fatty alcohol sulfate mixture prepared from naturally occurring fatty acids. These also include the salts of sulfuric acid esters and sulfonic acids of fatty alcohol-ethylene oxide adducts. The sulfonated benzimidazole derivatives preferably contain two sulfonic acid groups and a fatty acid radical having 8–22 C atoms. Alkylarylsulfonates are, for example, the Na, Ca or triethanolamine salts of dodecylbenzenesulfonic acid, of dibutylnaphthalenesulfonic acid or of a naphthalenesulfonic acid-formaldehyde condensation product.

The corresponding phosphates, for example salts of the phosphoric acid ester of a p-nonylphenol-(4–14)-ethylene oxide adduct, are furthermore also possible.

Possible non-ionic surfactants are, in particular, polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols.

Other suitable non-ionic surfactants are the water-soluble adducts, containing 20 to 250 ethylene glycol ether groups and 10 to 100 propylene glycol ether groups, of polyethylene oxide with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit.

Examples which may be mentioned of non-ionic surfactants are nonylphenol polyethoxyethanols, castor oil polyglycol ethers, polypropylene-polyethylene oxide adducts, tributylphenoxypolyethyleneethanol, polyethylene glycol and octylphenoxypolyethoxyethanol.

Fatty acid esters of polyoxyethylene sorbitan, such as polyoxyethylene sorbitan trioleate, are furthermore also possible.

The cationic surfactants are in particular quaternary ammonium salts which contain at least one alkyl radical having 8 to 22 C atoms as N substituents and contain lower non-halogenated or halogenated alkyl, benzyl or lower hydroxyalkyl radicals as further substituents. The salts are preferably in the form of halides, methyl sulfates or ethyl sulfates, for example stearyltrimethylammonium chloride or benzyldi(2-chloroethyl) ethylammonium bromide.

The surfactants conventionally used in the art of formulation are described, inter alia, in the following publications: "McCutcheon's Detergents and Emulsifiers Annual", MC Publishing Corp., Ridgewood, N.J., 1979; and Dr. Helmut Stache "Tensid Taschenbuch (Surfactant Handbook)", Carl Hanser Verlag, Munich-/Vienna.

The agrochemical preparations as a rule contain 0.1 to 99% by weight, in particular 0.1 to 95% by weight, of active substance of the formula I, 99.9 to 1% by weight, in particular 99.8 to 5% by weight, of a solid or liquid additive and 0 to 25% by weight, in particular 0.1 to 25% by weight, of a surfactant.

Whilst concentrated compositions are rather preferred as commercial products, the end user as a rule uses dilute compositions.

The compositions can also contain other additives, such as stabilizers, antifoam, viscosity regulators, binders, tackifiers and fertilizers, or other active substances for achieving special effects.

The present invention relates to such agrochemical compositions.

The examples which follow serve to illustrate the invention in more detail, without limiting it.

1. Preparation Examples

Example H1:
2-Mercapto-5-(2-methyl-1,3,4-oxadiazol-5-yl)-1,3,4-oxadiazole (Compound No. 1.5)

3.6 g of 5-methyl-1,3,4-oxadiazole-2-carboxylic acid hydrazide of melting point 150°–151° C., prepared in the customary manner from the corresponding ethyl ester [Canad.J.Chem. 65, 166 (1987)], are stirred in 100 ml of dioxane with 2.9 g of thiophosgene at room temperature overnight and then at 55° C. for 5 hours. After cooling, undissolved solids are filtered off and 200 ml of hexane are added to the filtrate, the desired product (4 g of decomposition point 225°) crystallizing out.

Example H2:
2-Mercapto-5-(2-dimethylamino-1,3,4-oxadiazol-5-yl)-1,3,4-oxadiazole (Compound No. 1.6)

8.5 g of 5-dimethylamino-oxadiazole-2-carboxylic acid hydrazide of melting point 151°–153° C., prepared in the customary manner from the corresponding ethyl ester (J.Heterocyclic Chem. 14, (1977) 1385), are stirred in 200 ml of dioxane with 5.7 g of thiophosgene at room temperature overnight and then at 70° for a further 4 hours. After the reaction mixture has been cooled to 20°, the solid components are filtered off with suction and stirred with water. After the crystals have been dried, the title compound (8.3 g) of melting point 227°–29° C. (decomposition) is obtained.

Example H3:
2-(3,4,4-Trifluoro-3-buten-1-ylthio)-5-(2-methyl-1,3,4-oxadiazol-5-yl)-1,3,4-oxadiazole (Compound No. 2.28)

3.7 g of 2-mercapto-5-(2-methyl-1,3,4-oxadiazol-5-yl)-1,3,4-oxadiazole according to Example H1 are initially introduced into a mixture of 36 ml of dioxane and 4 ml of dimethylformamide, and 2.24 g of potassium t-butylate are added, while stirring. 4.2 g of 4-bromo-1,1,2-trifluorobut-1-ene are added dropwise and the mixture is stirred overnight at room temperature. After the salts have been filtered off, the solvents are distilled off in vacuo, the residue is taken up in methylene chloride, the solution is washed with water and 1-normal sodium hydroxide solution in succession and the solvent is evaporated off in vacuo. 3.2 g of the desired compound of melting point 77°–79° C. are obtained as the residue.

Example H4:
2-(3,4,4-Trifluoro-3-buten-1-ylthio)-5-(2-dimethylamino-1,3,4-oxadiazol-5-yl)-1,3,4-oxadiazole (Compound No. 2.32)

4.26 g of 2-mercapto-5-(2-dimethylamino-1,3,4-oxadiazol-5-yl)-1,3,4-oxadiazole according to Example H2 are initially introduced into 40 ml of dioxane and stirred with 2.24 g of potassium t-butylate. 4 ml of dimethylformamide and then 4.2 g of 4-bromo-1,1,2-trifluorobut-1-ene are added and the mixture is stirred overnight at room temperature. The mixture is poured into water and the crystals are filtered off with suction. After drying and stirring with ether, 4.6 g of the title compound of melting point 87°–90° C. are obtained.

The following intermediates and compounds according to the invention can be prepared analogously to the preparation examples above and the processes already described. The compounds listed below serve to illustrate the present invention and do not represent a limitation thereof.

TABLE 1

(Intermediate product) (II)

$$R_2 - \underset{X_2}{\underset{\|}{\overset{N-N}{\diagup}}} - \underset{X_1}{\underset{\|}{\overset{N-N}{\diagup}}} - SH$$

| Comp. No. | $R_2$ | $X_2$ | $X_1$ | Physic. data |
|---|---|---|---|---|
| 1.1 | H | O | O | |
| 1.2 | H | O | S | |
| 1.3 | H | S | O | |
| 1.4 | H | S | S | |
| 1.5 | $CH_3$ | O | O | m.p.: 225–227° C. |
| 1.6 | $(CH_3)_2N$ | O | O | m.p.: 227–229° C. |
| 1.7 | $CH_3S$ | S | S | m.p.: 179–182° C. |
| 1.8 | $CH_3S$ | S | O | m.p.: 190–194° C. |
| 1.9 | $CH_3O$ | S | O | |
| 1.10 | $CH_3O$ | S | S | |
| 1.11 | $CHF_2S$ | S | O | |
| 1.12 | $CHF_2S$ | S | S | |
| 1.13 | SH | O | O | m.p.: 236–238° C. |
| 1.14 | $CH_3$ | O | S | m.p.: 204–207° C. |

TABLE 2

(I)

$$R_1S - \underset{X_1}{\underset{\|}{\overset{N-N}{\diagup}}} - \underset{X_2}{\underset{\|}{\overset{N-N}{\diagup}}} - R_2$$

| Comp. No. | $R_1$ | $R_2$ | $X_1$ | $X_2$ | Physic. data |
|---|---|---|---|---|---|
| 2.1 | $CH_3$ | H | O | O | |
| 2.2 | $CH_2CN$ | H | O | O | |
| 2.3 | $CH_2CN$ | H | O | S | |
| 2.4 | $CH_2CH=CH_2$ | H | O | O | |
| 2.5 | $CH_2CH=CH_2$ | H | O | S | |
| 2.6 | $CH_2-C\equiv CH$ | H | O | O | |
| 2.7 | $CH_2-C\equiv CH$ | H | O | S | |
| 2.8 | $CH_2-C\equiv CH$ | H | S | O | |
| 2.9 | $CH_2-C\equiv CH$ | H | S | S | |
| 2.10 | $CF_3$ | H | O | O | |
| 2.11 | $CF_3$ | H | O | S | |
| 2.12 | $CHF_2$ | H | O | O | |
| 2.13 | $CHF_2$ | H | O | S | |
| 2.14 | $CHF_2$ | H | S | O | |
| 2.15 | $CHF_2$ | H | S | S | |
| 2.16 | $CHF_2$ | $CH_3$ | O | O | |
| 2.17 | $CHF_2$ | $CH_3$ | O | S | |
| 2.18 | $CHF_2$ | $CH_3$ | S | O | m.p.: 103–106° C. |

TABLE 2-continued $$R_1S-\underset{X_1}{\overset{N-N}{\diagup\!\!\!\diagdown}}-\underset{X_2}{\overset{N-N}{\diagup\!\!\!\diagdown}}-R_2 \quad (I)$$

| Comp. No. | $R_1$ | $R_2$ | $X_1$ | $X_2$ | Physic. data |
|---|---|---|---|---|---|
| 2.19 | $CHF_2$ | $CH_3$ | S | S | |
| 2.20 | $CHF_2$ | $(CH_3)_2N$ | O | O | |
| 2.21 | $CHF_2$ | $(CH_3)_2N$ | O | S | |
| 2.22 | $CHF_2$ | $(CH_3)_2N$ | S | O | |
| 2.23 | $CHF_2$ | $(CH_3)_2N$ | S | S | |
| 2.24 | $CH_2-CH_2-CF=CF_2$ | H | O | O | |
| 2.25 | $CH_2-CH_2-CF=CF_2$ | H | O | S | |
| 2.26 | $CH_2-CH_2-CF=CF_2$ | H | S | O | |
| 2.27 | $CH_2-CH_2-CF=CF_2$ | H | S | S | |
| 2.28 | $CH_2-CH_2-CF=CF_2$ | $CH_3$ | O | O | m.p.: 77-79° C. |
| 2.29 | $CH_2-CH_2-CF=CF_2$ | $CH_3$ | O | S | |
| 2.30 | $CH_2-CH_2-CF=CF_2$ | $CH_3$ | S | O | m.p.: 69-71° C. |
| 2.31 | $CH_2-CH_2-CF=CF_2$ | $CH_3$ | S | S | |
| 2.32 | $CH_2-CH_2-CF=CF_2$ | $(CH_3)_2N$ | O | O | m.p.: 87-90° C. |
| 2.33 | $CH_2-CH_2-CF=CF_2$ | $(CH_3)_2N$ | O | S | |
| 2.34 | $CH_2-CH_2-CF=CF_2$ | $(CH_3)_2N$ | S | O | |
| 2.35 | $CH_2-CH_2-CF=CF_2$ | $(CH_3)_2N$ | S | S | |
| 2.36 | $CHF_2$ | $CH_3S$ | O | S | m.p.: 68-70° C. |
| 2.37 | $CHF_2$ | $CH_3S$ | S | S | m.p.: 100-102° C. |
| 2.38 | $CH_2-CH_2-CF=CF_2$ | $CH_3S$ | O | S | m.p.: 68-70° C. |
| 2.39 | $CH_2-CH_2-CF=CF_2$ | $CH_3S$ | S | S | m.p.: 93-97° C. |
| 2.40 | $CHF_2$ | $CH_3O$ | O | S | |
| 2.41 | $CHF_2$ | $CH_3O$ | S | S | |
| 2.42 | $CH_2-CH_2-CF=CF_2$ | $CH_3O$ | O | S | |
| 2.43 | $CH_2-CH_2-CF=CF_2$ | $CH_3O$ | S | S | |
| 2.44 | $CHF_2$ | $CHF_2S$ | O | S | |
| 2.45 | $CHF_2$ | $CHF_2S$ | S | S | |
| 2.46 | $CH_2-CH_2-CF=CF_2$ | $CHF_2S$ | O | S | |
| 2.47 | $CH_2-CH_2-CF=CF_2$ | $CHF_2S$ | S | S | |
| 2.48 | $CH_2-CH_2-CF=CF_2$ | SH | S | O | m.p. 132° C. (Zers.) |
| 2.49 | $CH_2-CH_2-CF=CF_2$ | $SCH_2-CH_2-CF=CF_2$ | S | O | oil |
| 2.50 | $CH_2-CH_2-CF=CF_2$ | $C_6H_5$ | S | O | m.p. 90-92° C. |
| 2.51 | H | $C_6H_5$ | S | O | m.p. 177-185° C. |
| 2.52 | H | $C_6H_5$ | O | O | Smp. 195° C. (Zers.) |
| 2.53 | $CH_2-CH_2-CF=CF_2$ | $C_6H_5$ | O | O | resin |
| 2.54 | $CHF_2$ | $C_6H_5$ | S | O | m.p. 132-134° C. |
| 2.55 | $CH_2-CH_2-CF=CF_2$ | $CHF_2S$ | S | O | oil |
| 2.56 | $CH_2-CH_2-CF=CF_2$ | SH | S | S | |
| 2.57 | $CH_2-CH_2-CF=CF_2$ | $CHF_2S$ | S | S | |
| 2.58 | $CH_2-CH_2-CF=CF_2$ | $SCH_2-CH_2-CF=CF_2$ | S | S | |
| 2.59 | $CH_2-CH_2-CF=CF_2$ | $SCH_2-CH_2-CF=CF_2$ | O | O | $n_D^{22}$ 1,5339 |

FORMULATION EXAMPLES

F.2. Formulation Examples for Liquid Active Substances of the Formula I (%=percent by weight)

| F.2.1 Emulsion concentrates | a) | b) | c) |
|---|---|---|---|
| Active substance from Table 2 | 25% | 40% | 50% |
| Ca dodecylbenzenesulfonate | 5% | 8% | 6% |
| Castor oil polyethylene glycol ether (36 mol of ethylene oxide) | 5% | — | — |
| Tributylphenol polyethylene glycol ether (30 mol of ethylene oxide) | — | 12% | 4% |
| Cyclohexanone | — | 15% | 20% |
| Xylene mixture | 65% | 25% | 20% |

Emulsions of any desired concentration can be prepared from those concentrates by dilution with water.

| F.2.2 Solutions | a) | b) | c) | d) |
|---|---|---|---|---|
| Active substance from Table 2 | 80% | 10% | 5% | 95% |
| Ethylene glycol monomethyl ether | 20% | — | — | — |
| Polyethylene glycol MW 400 | — | 70% | — | — |
| N-Methyl-2-pyrrolidone | — | 20% | — | — |
| Epoxidized coconut oil | — | — | 1% | 5% |
| Benzine (boiling limits 160-190° C.) | — | — | 94% | — |

(MW = molecular weight)

The solutions are suitable for use in the form of tiny drops.

| F.2.3 Granules | a) | b) |
|---|---|---|
| Active substance from Table 2 | 5% | 10% |
| Kaolin | 94% | — |
| Highly disperse silica | 1% | — |
| Attapulgite | — | 90% |

The active substance is dissolved in methylene chloride, the solution is sprayed onto the carrier and the solvent is then evaporated off in vacuo.

| F.2.4 Dusts | a) | b) |
|---|---|---|
| Active substance from Table 2 | 2% | 5% |
| Highly disperse silica | 1% | 5% |
| Talc | 97% | — |

-continued

| F.2.4 Dusts | a) | b) |
|---|---|---|
| Kaolin | — | 90% |

Ready-to-use dusts are obtained by intimate mixing of the carriers with the active substance.

| F.3.1 Wettable powders | a) | b) | c) |
|---|---|---|---|
| Active substance from Table 2 | 25% | 50% | 75% |
| Na lignosulfonate | 5% | 5% | — |
| Na lauryl sulfate | 3% | — | 5% |
| Na diisobutylnaphthalenesulfonate | — | 6% | 10% |
| Octylphenol polyethylene glycol ether (7-8 mol of ethylene oxide) | — | 2% | — |
| Highly disperse silica | 5% | 10% | 10% |
| Kaolin | 62% | 27% | — |

The active substance is mixed thoroughly with the additives and the mixture is ground thoroughly in a suitable mill. Wettable powders which can be diluted with water to give suspensions of any desired concentration are obtained.

| F.3.2 Emulsion concentrate | |
|---|---|
| Active substance from Table 2 | 10% |
| Octylphenol polyethylene glycol ether (4-5 mol of ethylene oxide) | 3% |
| Ca dodecylbenzenesulfonate | 3% |
| Castor oil polyglycol ether (35 mol of ethylene oxide) | 4% |
| Cyclohexanone | 30% |
| Xylene mixture | 50% |

Emulsions of any desired concentration can be prepared from this concentrate by dilution with water.

| F.3.3 Dusts | a) | b) |
|---|---|---|
| Active substance from Table 2 | 5% | 8% |
| Talc | 95% | — |
| Kaolin | — | 92% |

Ready-to-use dusts are obtained by mixing the active compound with the carriers and grinding the mixture on a suitable mill.

| F.3.4 Extruded granules | |
|---|---|
| Active substance from Table 2 | 10% |
| Na ligninsulfonate | 2% |
| Carboxymethylcellulose | 1% |
| Kaolin | 87% |

The active substance is mixed with the additives and the mixture is ground and moistened with water. This mixture is extruded and then dried in a stream of air.

| F.3.5 Coated granules | |
|---|---|
| Active substance from Table 2 | 3% |
| Polyethylene glycol (MW 200) | 3% |
| Kaolin | 94% |

(MW = molecular weight)

The finely ground active substance is uniformly applied to the kaolin moistened with polyethylene glycol in a mixer. Dust-free coated granules are obtained in this manner.

| F.3.6 Suspension concentrate | |
|---|---|
| Active substance from Table 2 | 40% |
| Ethylene glycol | 10% |
| Nonylphenol polyethylene glycol ether (15 mol of ethylene oxide) | 6% |
| Na ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active substance is intimately mixed with the additives. A suspension concentrate from which suspensions of any desired concentration can be prepared by dilution with water is thus obtained.

BIOLOGICAL EXAMPLES

B.1 Action against *Meloidogyne incognita* on Tomatoes

Eggs of *Meloidogyne incognita* are mixed into sand. This mixture is then introduced into clay pots of 200 ml capacity (5000 eggs per pot). The same day, one tomato plant 3 weeks old is planted per pot and the formulated active substance is introduced into the pot by means of drench application (0.0006% of active substance, based on the volume of soil). The potted plants are now placed in a greenhouse at a temperature of 26°±1° C. and a relative atmospheric humidity of 60%. After 4 weeks have elapsed, evaluation is performed by examining the plants for root knot formation in accordance with the so-called root knot index.

Compounds from Table 2 have a good activity against *Meloidogyne incognita* as shown by substantial reduction of root knot formation. In contrast, untreated but infected control plants show extensive root knot formation (=100%). Thus, for example, compounds No. 2.28, 2.37, 2.38 and 2.39 inhibit root knot formation most completely in the above experiment (0-10% residual infestation).

B.2 Action against *Cercospora arachidicola* on Peanut Plants

Residual-protective Action

Peanut plants 10-15 cm high are sprayed with a spray liquor prepared from a wettable powder of the active substance (200 ppm of active substance) and 48 hours later are infected with a conidia suspension of the fungus. The infected plants are incubated for 72 hours at about 21° C. and high atmospheric humidity and are then placed in a greenhouse until the typical leaf spots appear. The fungicidal action is evaluated 12 days after infection and is based on the number and size of spots which appear.

In comparison with untreated but infected control plants (number and size of the spots=100%), peanut plants which are treated with active substances from the table show a greatly reduced *Cercospora* infestation. Compound 2.38 prevents the appearance of spots almost completely (0-10%).

B.3 Action against *Plasmopara viticola* on Vines a) Residual-protective Action

Vine seedlings in the 4-5 leaf stage were sprayed with a spray liquor prepared from a wettable powder of the active substance (200 ppm of active substance). After 24 hours, the treated plants were infected with a sporangia suspension of the fungus. After incubation for 6 days at a relative atmospheric humidity of 95-100% and 20° C., the fungal infestation was evaluated.

b) Residual-curative Action

Vine seedlings in the 4-5 leaf stage were infected with a sporangia suspension of the fungus. After incubation for 24 hours in a humidity chamber at 95-100% relative atmospheric humidity and 20° C., the infected plants were dried and sprayed with a spray liquor prepared from a wettable powder of the active substance (0.06% of active substance). After the spray coating had dried on, the treated plants were again placed in the humidity chamber. The fungal infestation was evaluated 6 days after the infection.

Compounds from Tables 1 and 2 showed a very good fungicidal action against Plasmopara viticola on vines, and in particular active substance No. 2.37 effected complete suppression of the fungal infestation (residual infestation 0 to 5%).

B.4 Action against *Rhizoctonia solani* (Soil Fungus on Rice Plants)

Protective-local Soil Application

Rice plants 12 days old are watered with a spray liquor prepared from a formulation of the active substance (0.002% of active substance), without contaminating above-ground parts of plants. To infect the treated plants, a suspension of the mycelium and sclerotia of R. solani is introduced onto the soil surface. After incubation for 6 days at 27° C. (daytime) and 23° C. (nighttime) and 100% relative atmospheric humidity (humidity boxes) in a climatically controlled chamber, the fungal infestation on the leaf sheath, leaves and stem is evaluated. Compounds from Tables 1-2 have a good activity against *Rhizoctonia solani*. Thus, compound 2.37 has about 80% efficiency.

B.5 Action against *Phytophthora infestans* on Tomato Plants a) After being grown for 3 weeks, tomato plants are sprayed with a spray liquor prepared from a wettable powder of the active substance (0.02% of active substance). After 24 hours, the treated plants are infected with a sporangia suspension of the fungus. The fungal infestation was evaluated after incubation of the infected plants at a relative atmospheric humidity of 90-100% and 20° C. for 5 days.

b) After tomato plants have been grown for 3 weeks, they are watered with a spray liquor prepared from a wettable powder of the active substance (0.006% of active substance, based on the volume of soil). It is ensured here that the spray liquor does not come into contact with the above-ground parts of plants. After 48 hours, the treated plants are infected with a sporangia suspension of the fungus. The fungal infestation is evaluated after incubation of the infected plants at a relative atmospheric humidity of 90-100% and 20° C. for 5 days.

Compounds from Tables 1-2 showed a good protective action against the Phytophthora fungus. Thus, for example, compound 2.37 reduced the fungal infestation to 0 to 20%. In contrast, untreated but infected control plants showed 100% Phytophthora infestation.

B.6 Action against *Erysiphe graminis* on Barley a) Residual-protective Action

Barley plants about 8 cm high were sprayed with a spray liquor prepared from a wettable powder of the active substance (0.02% of active substance). After 3-4 hours, the treated plants were dusted with conidia of the fungus. The infected barley plants were placed in a greenhouse at about 22° C. and the fungal infestation was evaluated after 10 days.

b) Systemic Action

Barley plants about 8 cm high were watered with a spray liquor prepared from a wettable powder of the active substance (0.002% of active substance, based on the soil volume). It was ensured here that the spray liquor did not come into contact with the above-ground parts of plants. After 48 hours, the treated plants were dusted with conidia of the fungus. The infected barley plants were placed in a greenhouse at about 22° C. and the fungal infestation was evaluated after 10 days.

Compounds from Tables 1-2 had a good action against Erysiphe fungi. Untreated but infected control plants showed an *Erysiphe infestation* of 100%. Amongst other compounds from the tables, compound No. 2.36 inhibited the fungal infestation on barley to 0-5%.

What is claimed is:

1. A mercapto-bis-(1,3,4-oxa- or -thiadiazole) of the formula I

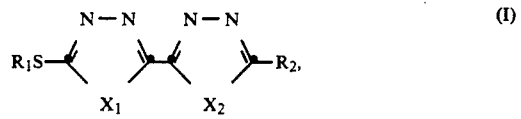

in which
X₁ and X₂ independently of one another are oxygen or sulfur,
R₁ is hydrogen or C₁-C₅alkyl which is unsubstituted or substituted by halogen, C₁-C₃alkoxy or cyano; C₃-C₇alkenyl which is unsubstituted or substituted by halogen; or C₃-C₇alkynyl which is unsubstituted or substituted by halogen,
R₂ is hydrogen, C₁-C₅alkyl, C₁-C₃alkoxy which is unsubstituted or substituted by halogen, C₁-C₃alkylthio which is unsubstituted or substituted by halogen, C₃-C₇alkenylthio which is unsubstituted or substituted by halogen, C₃-C₇alkynylthio which is unsubstituted or substituted by halogen, —SH, phenyl which is unsubstituted or substituted by halogen or

in which R₃ and R₄ are C₁-C₃alkyl, and a salt of this compound.

2. A mercapto-bis-(1,3,4-oxa- or -thiadiazole) according to claim 1, in which
R₁ is C₁-C₅alkyl which is unsubstituted or substituted by halogen, C₁-C₃alkoxy or cyano; C₃-C₇alkenyl which is unsubstituted or substituted by halogen; or C₃-C₇alkynyl which is unsubstituted or substituted by halogen, $R_2$ is hydrogen, $C_1$–$C_5$alkyl, $C_1$–$C_3$alkoxy which is unsubstituted or substituted by halogen, $C_1$–$C_3$alkylthio which is unsubstituted or substituted by halogen, $C_3$–$C_7$alkenylthio which is unsubstituted or substituted by halogen, $C_3$–$C_7$alkynylthio which is unsubstituted or substituted by halogen, —SH, phenyl which is unsubstituted or substituted by halogen or

in which $R_3$ and $R_4$ are $C_1$–$C_3$alkyl, or a salt of this compound.

3. A mercapto-bis-(1,3,4-oxa- or -thiadiazole) according to claim 2, in which $X_1$ and $X_2$ independently of one another are oxygen or sulfur, $R_1$ is $C_1$–$C_5$alkyl which is unsubstituted or substituted by halogen, $C_1$–$C_3$alkoxy or cyano; $C_3$–$C_7$alkenyl which is unsubstituted or substituted by halogen; or $C_3$–$C_7$alkynyl which is unsubstituted or substituted by halogen and $R_2$ is hydrogen, $C_1$–$C_5$alkyl or

in which $R_3$ and $R_4$ are $C_1$–$C_3$alkyl, and $R_4$ a salt of this compound.

4. A 2-mercapto-5-(1,3,4-oxadiazol-5-yl)-1,3,4-oxadiazole of the formula Ia

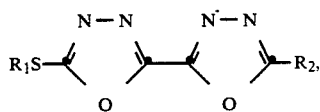

according to claim 3, in which $R_1$ is methyl, difluoromethyl, trifluoromethyl, cyanomethyl, allyl, propargyl or 3,4,4-trifluoro-3-buten-1-yl and $R_2$ is hydrogen, methyl or dimethylamino.

5. A 2-mercapto-5-(1,3,4-oxadiazol-5-yl)-1,3,4-oxadiazole according to claim 4, in which $R_1$ is difluoromethyl or 3,4,4-trifluoro-3-buten-1-yl.

6. 2-Difluoromethylthio-5-(2-methyl-1,3,4-oxadiazol-5-yl)-1,3,4-oxadiazole according to claim 5.

7. 2-(3,4,4-Trifluoro-3-buten-1-ylthio)-5-(2-methyl-1,3,4-oxadiazol-5-yl)-1,3,4-oxadiazole according to claim 5.

8. A 2-mercapto-5-(1,3,4-thiadiazol-5-yl)-1,3,4-oxadiazole of the formula Ib

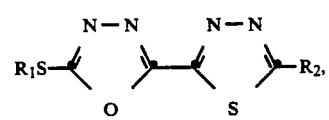

according to claim 3, in which -$R_1$ is methyl, difluoromethyl, trifluoromethyl, cyanomethyl, allyl, propargyl or 3,4,4-trifluoro-3-buten-1-yl and $R_2$ is hydrogen, methyl or dimethylamino.

9. 2-Difluoromethylthio-5-(2-methyl-1,3,4-oxadiazol-5-yl)-1,3,4-thiadiazole according to claim 8.

10. 2-(3,4,4-Trifluoro-3-buten-1-ylthio)-5-(2-methyl-1,3,4-oxadiazol-5-yl)-1,3,4-thiadiazole according to claim 8.

11. A 2-mercapto-5-(1,3,4-oxadiazol-5-yl)-1,3,4-thiadiazole of the formula Ic

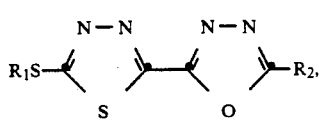

according to claim 3, in which $R_1$ is methyl, difluoromethyl, trifluoromethyl, cyanomethyl, allyl, propargyl or 3,4,4-trifluoro-3-buten-1-yl and $R_2$ is hydrogen, methyl or dimethylamino.

12. A 2-mercapto-5-(1,3,4-oxadiazol-5-yl)-1,3,4-thiadiazole of the formula Id

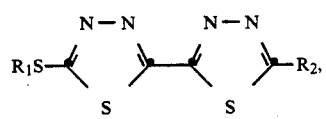

according to claim 3, in which $R_1$ is methyl, difluoromethyl, trifluoromethyl, cyanomethyl, allyl, propargyl or 3,4,4-trifluoro-3-buten-1-yl and $R_2$ is hydrogen, methyl or dimethylamino.

13. 2-(3,4,4-Trifluoro-3-buten-1-ylthio)-5-(2-methylthio-1,3,4-thiadiazol-5-yl)-1,3,4-thiadiazole according to claim 2.

14. 2-(3,4,4-Trifluoro-3-buten-1-ylthio)-5-(2-methylthio-1,3,4-thiadiazol-5-yl)-1,3,4-oxadiazole according to claim 2.

15. 2-(Difluoromethylthio)-5-(2-methyl-1,3,4-oxadiazol-5-yl)-1,3,4-thiadiazole according to claim 11.

16. 2-(3,4,4-Trifluoro-3-buten-1-ylthio)-5-(2-methyl-1,3,4-oxadiazol-5-yl)-1,3,4-thiadiazole according to claim 11.

17. A compound according to claim 1, in which $R_1$ is difluoromethylthio or 3,4,4-trifluoro-3-buten-1-yl and $R_2$ is difluoromethylthio, 3,4,4-trifluoro-3-buten-1-yl or the thiol radical.

18. 2-(3,4,4-Trifluoro-3-buten-1-ylthio)-5-(2-mercapto-1,3,4-oxadiazol-5-yl)-1,3,4-thiadiazole according to claim 11.

19. 2-(3,4,4-Trifluoro-3-buten-1-ylthio)-5-1,3,4-thiadiazole according to claim 11.

20. 2-(3,4,4-Trifluoro-3-buten-1-ylthio)-5-(2-phenyl-1,3,4-oxadiazol-5-yl)-1,3,4-thiadiazole according to claim 11.

21. 2-(3,4,4-Trifluoro-3-buten-1-ylthio)-5-(2-phenyl-1,3,4-oxadiazol-5-yl)-1,3,4-oxadiazole according to claim 11.

22. 2-(3,4,4-Trifluoro-3-buten-1-ylthio)-5-(2-difluoromethylthio-1,3,4-oxadiazol-5-yl)-1,3,4-thiadiazole according to claim 11.

23. 2-(3,4,4-Trifluoro-3-buten-1-ylthio)-5-1,3,4-oxadiazole according to claim 11.

24. A compound of the formula IIa

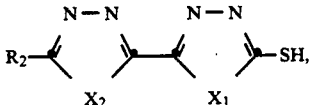

in which $R_2$, $X_1$ and $X_2$ are as defined according to claim 1 under formula I, with the proviso that $R_2$ is other than hydrogen if $X_1$ and $X_2$ are sulfur.

25. A compound of the formula IIa,

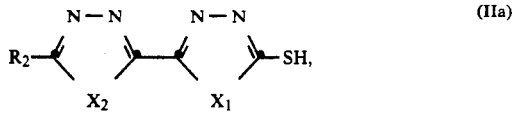

wherein $R_2$, $X_1$ and $X_2$ are as defined according to claim 1 under formula I, with the proviso that $X_1$ and $X_2$ are not simultaneously sulfur.

26. A pest control composition for controlling or preventing infestation of plants by nematodes and fungi, which contains at least one compound of the formula I according to claim 1 as the active component.

27. A composition according to claim 26, which contains 2-difluoromethylthio-5-(2-methyl-1,3,4-oxadiazol-5-yl)-1,3,4-oxadiazole as the active component.

28. A composition according to claim 26, which contains 2-(3,4,4-trifluoro-3-buten-1-ylthio)-5-(2-methyl-1,3,4-oxadiazol-5-yl)-1,3,4-oxadiazole as the active component.

29. A composition according to claim 26, which contains 2-difluoromethylthio-5-(2-methyl-1,3,4-oxadiazol-5-yl)-1,3,4-thiadiazole as the active component.

30. A composition according to claim 26, which contains 2-(3,4,4-trifluoro-3-buten-1-ylthio)-5-(2-methyl-1,3,4-oxadiazol-5-yl)-1,3,4-thiadiazole as the active component.

31. A composition according to claim 29, which contains 0.1 to 95% of an active substance of the formula I, 99.8 to 5% of a solid or liquid additive and 0.1 to 25% of a surfactant.

32. A composition of claim 26 wherein $R_1$ is $C_1$-$C_5$alkyl which is unsubstituted or substituted by halogen, $C_1$-$C_3$alkoxy or cyano; $C_3$-$C_7$alkenyl which is unsubstituted or substituted by halogen; or $C_3$-$C_7$alkynyl which is unsubstituted or substituted by halogen, $R_2$ is hydrogen, $C_1$-$C_5$alkyl, $C_1$-$C_3$alkoxy which is unsubstituted or substituted by halogen, $C_1$-$C_3$alkylthio which is unsubstituted or substituted by halogen, $C_3$-$C_7$alkenylthio which is unsubstituted or substituted by halogen, $C_3$-$C_7$alkynylthio which is unsubstituted or substituted by halogen, $R_2$ is also —SH, phenyl which is unsubstituted or substituted by halogen or $R_2$

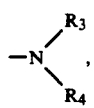

in which $R_3$ and $R_4$ are $C_1$-$C_3$, or a salt of this compound.

33. A composition of claim 32 wherein $R_2$ is hydrogen, $C_1$-$C_5$-alkyl or

34. A composition according to claim 26 which contains 0.1 to 99% of an active substance of the formula I, 99.9 to 1% of a solid or liquid additive and 0 to 25% of a surfactant.

35. A method of controlling or preventing infestation of crop plants by nematodes and fungi, which comprises applying a compound of the formula I according to claim 1 onto the plants or their location.

36. A method of claim 35 wherein $R_1$ is $C_1$-$C_5$alkyl which is unsubstituted or substituted by halogen, $C_1$-$C_3$alkoxy or cyano; $C_3$-$C_7$alkenyl which is unsubstituted or substituted by halogen; or $C_3$-$C_7$alkynyl which is unsubstituted or substituted by halogen, $R_2$ is hydrogen, $C_1$-$C_5$alkyl, $C_1$-$C_3$alkoxy which is unsubstituted or substituted by halogen, $C_1$-$C_3$alkylthio which is unsubstituted or substituted by halogen, $C_3$-$C_7$alkenylthio which is unsubstituted or substituted by halogen, $C_3$-$C_7$alkynylthio which is unsubstituted or substituted by halogen, $R_2$ is also —SH, phenyl which is unsubstituted or substituted by halogen or $R_2$

in which $R_3$ and $R_4$ are $C_1$-$C_3$, or a salt of this compound.

37. A method of claim 36 wherein $R_2$ is hydrogen, $C_1$-$C_5$alkyl or

38. A method according to claim 36, wherein the nematodes are species which are parasitic to plants.

39. A method according to claim 38 against nematodes of the genus Meloidogyne, Heterodera or Globodera.

40. A method according to claim 35 against fungi of the genera Pythium, Rhizoctonia, Fungi imperfecti, Basidomycetes, Ascomycetes and Oomycetes.

* * * * *